US005925654A

United States Patent [19]

Chen et al.

[11] Patent Number: 5,925,654

[45] Date of Patent: Jul. 20, 1999

[54] $LTA_4$, HYDROLASE INHIBITORS

[75] Inventors: Barbara Baosheng Chen, Glenview, Ill.; Helen Chen, Livingston, N.J.; Mark Andrew Russell, Gurnee, Ill.; Julie Marion Miyashiro, Chicago, Ill.; James Malecha, Libertyville, Ill.; Thomas Dale Penning, Emhurst, Ill.

[73] Assignee: G.D. Searle & Co., Skokie, Ill.

[21] Appl. No.: 08/815,696

[22] Filed: Mar. 12, 1997

[51] Int. Cl.[6] .................... C07D 207/08; C07D 207/325; A61K 31/40

[52] U.S. Cl. .......................... 514/326; 514/422; 514/423; 514/427; 514/428; 514/429; 546/213; 548/518; 548/531; 548/537; 548/561; 548/565

[58] Field of Search .................................... 514/326, 422, 514/423, 427, 428, 429; 546/213; 548/518, 531, 537, 561, 565

[56] References Cited

U.S. PATENT DOCUMENTS 5,700,816 12/1997 Isakson et al. .......................... 514/326

FOREIGN PATENT DOCUMENTS

| | | |
|---|---|---|
| 287959 | 10/1988 | European Pat. Off. . |
| 4121849 | 1/1993 | Germany . |
| WO9610999 | 4/1996 | WIPO . |
| WO9611192 | 4/1996 | WIPO . |
| WO9641625 | 12/1996 | WIPO . |

OTHER PUBLICATIONS

Chem. Abstracts, vol. 117(11), Abstr. No. 111411, Sep. 14, 1992.

Yuan et al., Chem. Abstracts, vol. 126(1), Abstr. No. 302, Jan.1, 1997.

Cavallini et al., Chem. Abstracts, vol. 53(10), Abstr. No. 9194, May 25, 1959.

Labaudiniere, R. et al., J. Med. Chem., vol. 35 (17), pp. 3156–3169 (1992).

*Primary Examiner*—Mukund J. Shah
*Assistant Examiner*—Deepak R. Rao
*Attorney, Agent, or Firm*—Fitzpatrick, Cella, Harper & Scinto

[57] ABSTRACT

The present invention provides compounds having the structure:

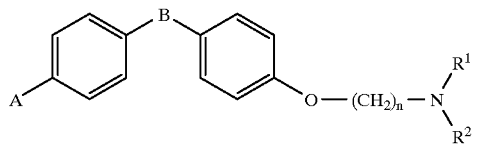

and pharmaceutically acceptable salts and stereoisomers thereof that are useful in the treatment of inflammatory diseases which are mediated by $LTB_4$ production, such as psoriasis, ulcerative colitis, IBD, and asthma.

9 Claims, No Drawings

LTA$_4$ , HYDROLASE INHIBITORS

FIELD OF THE INVENTION

This invention relates generally to anti-inflammatory compounds and pharmaceutical compositions, and more particularly to anti-inflammatory compounds and compositions which are capable of inhibiting leukotriene $A_4$ hydrolase.

BACKGROUND OF THE INVENTION

LTA$_4$ hydrolase is a requisite enzyme in the biosynthetic pathway leading to LTB$_4$ formation. LTB$_4$ is a proinflammatory compound. R. Lewis, et al., *N. Engl. J. Med.* 323, 645–655 (1990) have demonstrated that LTB$_4$ is a potent granulocyte agonist inducing chemotaxis, aggregation, degranulation, adherence and priming of inflammatory cells for induction by other agonists. Binding of LTB$_4$ to receptors is stereospecific with two distinct classes of binding sites. A. Lin, et al., *Prostaglandins* 28, 837–849 (1984). A high affinity site [$4–5\times10^{-10}$ M] mediates chemotaxis and chemokinesis while lower affinity sites [$0.6–5\times10^{-7}$ M] stimulate granular secretion and oxidative burst. The LTB$_4$ receptor is associated with a GTP-binding protein that regulates affinity and transduces signals. T. Schepers, et al., *J. Biol. Chem.* 267, 159–165 (1992). Elevated LTB$_4$ levels have been reported for many diseases. Most prominently, elevated LTB$_4$ levels have been correlated to the pathology of inflammatory bowel disease (IBD) including Crohn's disease and ulcerative colitis and in psoriasis. P. Sharon, et al., *Gastroent.* 86, 453–460; K. Lauritsen, et al., *Gastroent.* 95, 11–17 (1989); S. Brain, et al., *Br. J. Pharm.*, 83, 313–317 (1984). Other properties of LTB$_4$ which may contribute to disease processes are: stimulation of mucus secretion; stimulation of cytokine production; and the ability to act synergistically with other inflammatory mediators such as prostaglandins and cysteinyl leukotrienes thereby amplifying the inflammatory process.

B. Samuelsson, et al., *J. Biol Chem.*, 264, 19469–19472 (1989) have shown that LTB$_4$ biosynthesis from arachidonic acid involves the action of 2 enzymes, 5-lipoxygenase [5-LO] and LTA$_4$ hydrolase. 5-LO transforms arachidonic acid to 5-HPETE and subsequent formation of LTA$_4$, which is an unstable allylic epoxide intermediate which is enzymatically hydrolyzed by LTA$_4$ hydrolase to form the dihydroxy acid LTB$_4$.

LTA$_4$ hydrolase is distinct from cytosolic and microsomal epoxide hydrolases based on strict substrate requirements, product formation [5(S),12(R) vs. 5(S),6(R)] for mouse liver cytosolic epoxide hydrolase, and lack of inhibition by inhibitors of cytosolic epoxide hydrolase. LTA$_4$ hydrolase appears to be ubiquitously distributed in mammalian tissues even in cell types that do not express 5-LO, suggesting the importance of transcellular metabolism of LTA$_4$. While peptidomimetic compounds such as bestatin and captopril have been shown to exhibit LTA$_4$ hydrolase inhibitory activity, they are not able to satisfy the requirement of a small organic compound which is capable of cellular penetration. It would therefore be very advantageous to be able to provide low molecular weight inhibitors of LTB$_4$ biosynthesis which preferably exhibit oral activity in vivo at desirably low concentrations.

SUMMARY OF THE INVENTION

Applicants have now discovered that compounds having the structure:

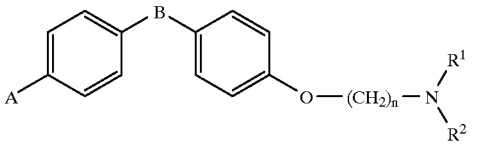

and pharmaceutically acceptable salts and stereoisomers thereof possess LTA$_4$ hydrolase inhibitor activity wherein A is

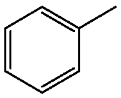

or

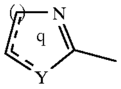

wherein

..... represents a single or double bond q is 1 or 2, and

Y is —O—, —S—, —$CH_2$—, or —CH—

B is —O—, —$CH_2$— or —$CH_2O$— n is an integer from 2 to 4

$R^1$ is H or $C_1$ to $C_4$ alkyl $R^2$ is $(CH_2)_m$ $R^3$ wherein m is an integer from 1 to 3

$R^3$ is $CO_2R^4$ $R^4$ is H alkyl, amino, alkylamino, dialkylamino or $NR^1R^2$ is combined to form

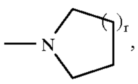

,

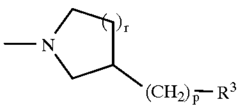

or

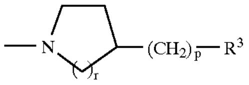

wherein r is 1 or 2, p is 0 to 3 and $R^3$ is as defined above.

DETAILED DESCRIPTION

In one of its embodiments, the present invention entails compounds having the structure:

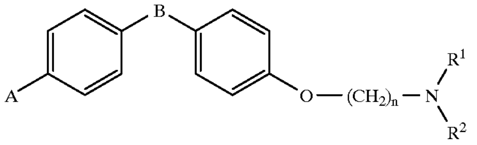

and pharmaceutically acceptable salts and stereoisomers thereof, wherein A, B, $R^1$, $R^2$, and n are as defined above.

The compounds of the present invention, in several embodiments, may comprise a carboxylic acid or ester moiety. It will be appreciated by those of ordinary skill in the art that a compound of the present invention comprising an ester moiety is readily converted, in vivo, especially when administered orally, into its corresponding carboxylic acid form. The ester-containing compounds of the present invention are therefore prodrugs of their carboxylic acid form.

In another of its aspects, the invention entails pharmaceutical composition comprising a pharmacologically effective amount of at least one of the compounds defined above and a pharmaceutically acceptable carrier.

In still another of its embodiments the present invention involves a method for treating a mammal exhibiting an LTB4 mediated inflammatory condition comprising administering to the mammal a pharmacologically effective amount of a compound of the invention.

The term "lower alkyl" means straight or branched chain alkyl having 1 to 6 carbon atoms such as methyl, ethyl, propyl, butyl, pentyl, hexyl and the branched chain isomers thereof. The term "lower alkoxy" means straight or branched chain alkoxy having 1 to 6 carbon atoms such as methoxy, ethoxy, propoxy, butoxy, pentoxy, hexoxy and the branched chain isomers thereof. The term "allyl" as used herein means the 1-propenyl radical, $—CH_2—CH_2═CH_2$. The term "halo" or "halogen" means fluoro, chloro, bromo, or iodo.

Included within the classes and subclasses of compounds embraced by this invention are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures disclosed herein a bond drawn across a bond in a ring indicates that the bond can be to any available atom of the ring structure.

The expression "pharmaceutically acceptable salts" is intended to include those salts capable of being formed with the compounds of the present invention without materially altering the chemical structure or pharmacological properties thereof. Such salts can be inorganic and organic cations or acid addition salts, including, but not limited to sodium, potassium, calcium, ammonium, alkylammonium, quaternary ammonium, triethanolamine, lysine, hydrochloride, hydrobromide, and others well known to those of ordinary skill in the art. The foregoing salts are prepared in the conventional manner by neutralization of the compounds of this invention with the desired base or acid.

The compounds of the present invention can be administered to a subject in such oral dosage forms as tablets, capsules, pills, powders, granules, elixirs or syrups, as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex and medical condition of the patient; the severity of the condition to be ameliorated; and the route of administration. A physician of ordinary skill can readily determine and prescribe a "pharmaceutically effective amount" of at least one of the compounds defined above, that is, the effective amount of the compound required to prevent, treat or arrest the progress of the condition. Dosages of the compounds of the present invention will range generally between 0.1 mg/kg/day to about 100 mg/kg/day and preferably between about 0.5 mg/kg/day to about 50 mg/kg/day when administered to subjects suffering from allergic or hypersensitivity reactions or inflammation. The compounds may also be administered transdermally or topically to treat proliferative skin conditions such as psoriasis. The daily dosage may be administered in a single dose or in equal divided doses, for example, three to four times daily. The subject is typically a mammal and, in particular, a human patient.

As used herein the phrase "$LTA_4$ hydrolase inhibitor" means a compound that is capable of exhibiting an $IC_{50}$ of less than 1 mM in an in vitro assay employing 10 $\mu$g/ml of $LTA_4$ hydrolase enzyme (specific activity 600 nMoles $LTB_4$/min/mg of enzyme) in the presence of 25 $\mu$M substrate ($LTA_4$) in a total reaction volume of 100 $\mu$l.

In the pharmaceutical compositions and methods of the present invention, at least one of the active compounds of the invention or a pharmaceutically acceptable salt thereof will typically be administered in admixture with suitable pharmaceutical diluents, excipients or carriers (collectively referred to herein as "carrier materials") suitably selected with respect to the intended form of administration and consistent with conventional pharmaceutical practices. For example, the pharmaceutical compositions of this inventio ncan be administered as oral tablets, capsules, elixirs, syrups and the like For oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Lubricants for use in these dosage forms include boric acid, sodium benzoate, sodium acetate, sodium chloride and the like. Disintegrators include, without limitation, starch, methylcellulose, agar, bentonite, guar gum and the like.

By virtue of their activity as $LTA_4$ hydrolase inhibitors, the compounds of the invention are useful in treating inflammatory conditions mediated by $LTB_4$ production in mammals such as psoriasis, contact and atrophic dermatitis, Crohn's disease, ulcerative colitis, inflammatory bowel disease, multiple sclerosis, ankylosing spondylitis, arthritis, asthma and the like. Similarly, the compounds of the invention can be used in preventing recurring inflammatory attacks. A physician or veterinarian of ordinary skill can readily determine whether a subject exhibits the inflammatory condition. A preferred utility relates to treatment of ulcerative colitis.

The compounds of the invention are prepared from readily available starting materials by any of the following alternate processes in a conventional manner. The following reaction schemes describe methods which can be employed for preparing the compounds of the invention including starting materials, intermediates and reaction conditions. The following terms, as used herein, have the following definitions:

| | |
|---|---|
| NMMO | N-methylmorpholine-N-oxide |
| Me | methyl |
| $SitBuMe_2$ | t-butyldimethylsilyl |
| nBuLi | n-butyllithium |
| THF | tetrahydrofuran |
| $Et_2O$ | diethyl ether |
| EtOH | ethyl alcohol |

-continued

| | |
|---|---|
| Pd/C | palladium on carbon |
| TFA | trifluoroacetic acid |
| $Et_3SiH$ | triethylsilane |
| TBAF | tetrabutylammonium fluoride |
| DMF | dimethylformamide |
| $nBu_4NBr$ | tetra-n-butylammonium bromide |
| TsCl | tosylchloride or p-toluenesulfonyl-chloride |
| TsO | tosylate or p-toluenesulfonate |
| MeOH | methyl alcohol |
| AcOH | acetic acid |
| Bn | benzyl |
| DEAD | diethylazodicarboxylate |
| $Ph_3P$ | triphenylphosphine |
| MCPBA | metachloroperbenzoic acid |
| LAH | lithium aluminum hydride |
| TsOH | tosic acid or p-toluenesulfonic acid |
| LDA | lithium diisopropylamide |
| DSC | disuccinylcarbonate |
| nBuOH | n-butyl alcohol |
| TFAA | trifluoroacetic anhydride |
| $Me_3SnN_3$ | trimethyl-tin azide |

-continued

| | |
|---|---|
| TMS | trimethyl silyl |
| $Ac_2O$ | acetic anhydride |
| Ac | acetate |
| EtOAc | ethyl acetate |
| Hep | heptane |

General Scheme

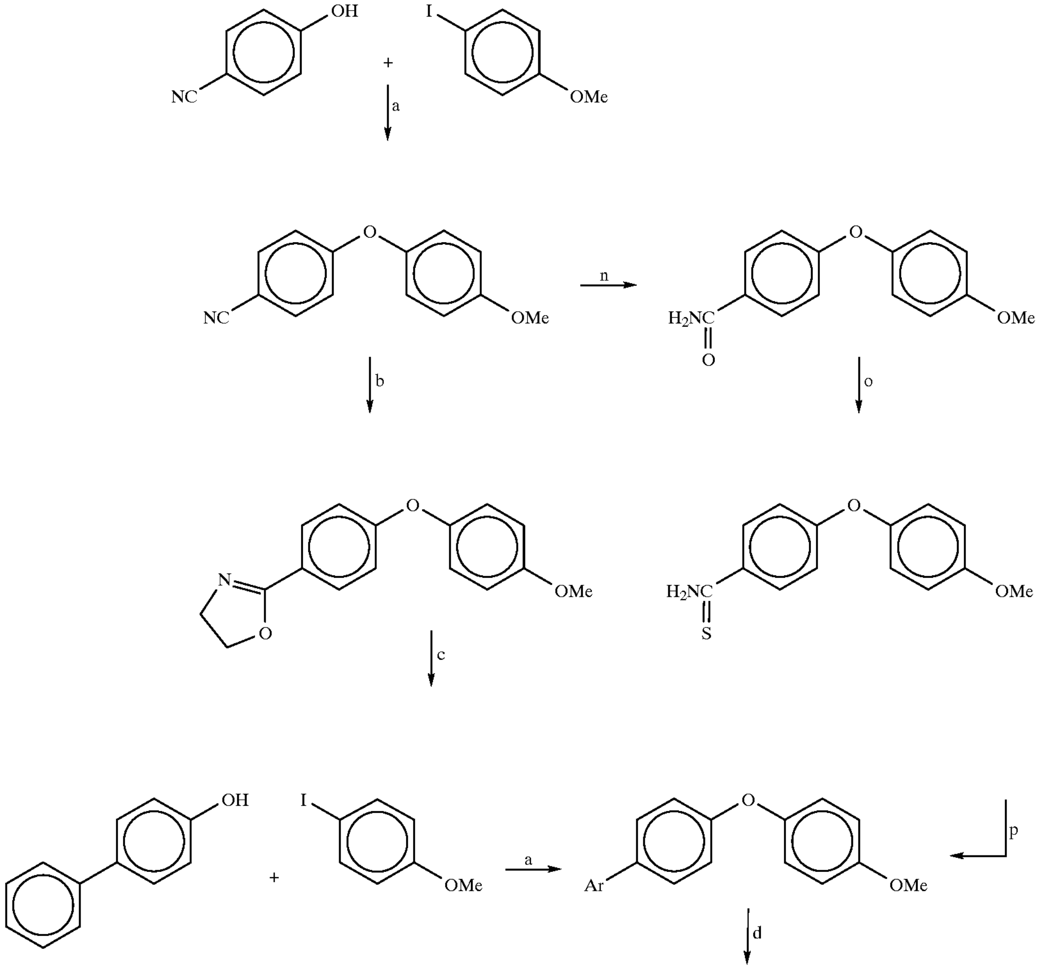

-continued
General Scheme
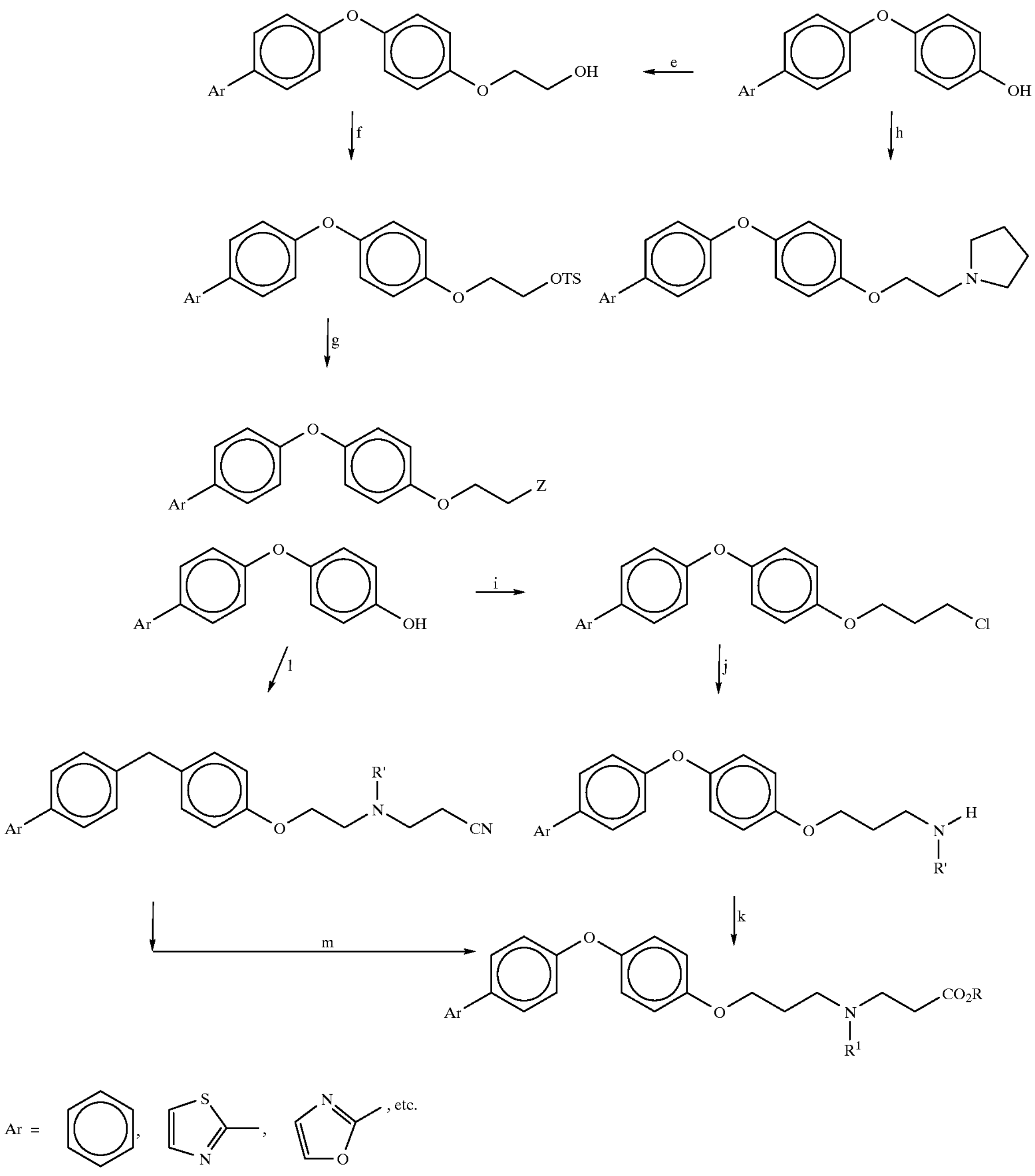
a) KOH, Cu°, 160° C.–200° C.
b) $ZnCl_2$, ethanolamine, 130° C.
c) $NiO_2$, benzene, reflux
d) $CH_2Cl_2$, $BBr_3$, −78° C.
e) Ethylene carbonate, DMF, $nBu_4NBr$, 140° C.
f) TsCl, pyridine, $CH_2Cl_2$, 0° C.
g) DMF, $K_2CO_3$, ZH, where Z is $NR^1R^2$ wherein $R^1$ and $R^2$ are as defined hereinbefore
h)
DMF, $K_2CO_3$,
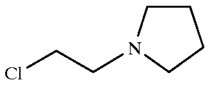
HCl, 80° C.

-continued

General Scheme i)

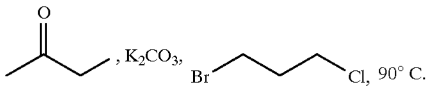

j) $CH_3CN$, $H_2NR'$, 55° C.

k) $CH_2Cl_2$, methylacrylate, room temp.

l)

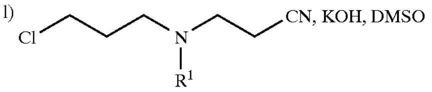

m) HCl n) KOH, DMSO, tBuOH, reflux o) Lawesson's reagent, toluene, reflux p) $(CO_2H)_2$, $ClCH_2CH(OMe)_2$, reflux

EXAMPLE 1

(c)

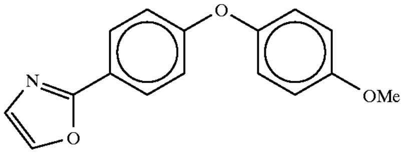

(a)

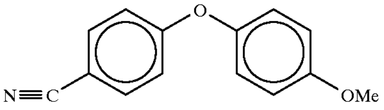

(a) A mixture of 4-iodobenzonitrile (5.06 g, 22 mmol), 4-methoxyphenol (2.72 g, 22 mmol), potassium carbonate (3.182 g, 22 mmol), and copper bronze (1.39, 22 mmol) in pyridine (120 ml) was heated to reflux under argon for 4 days. The reaction was allowed to cool to room temperature and concentrated in vacuo. The brown residue was acidified to pH=1 with concentrated HCl and diluted with water. The mixture was extracted with EtOAc (2X) and the organic layers collected. The organic layer was dried over $MgSO_4$ and concentrated in vacuo to give a black/brown solid (4.56 g). The solid was purified by column chromatography (5% EtOAc/hexane followed by 10% EtOAc/hexane) to give a white solid (1.8 g). NMR spectrum is consistent with structure (a) above.

(b)

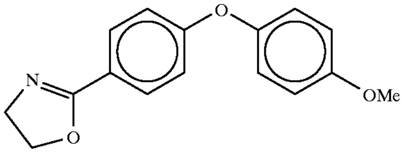

(b) A mixture of fused $ZnCl_2$ (0.782 g, 5.3 mmol), the compound from step a (0.548 g, 2.2 mmol), and ethanolamine (15 ml) was heated to 130–140° C. for 4 hours The reaction was diluted with $CH_2Cl_2$, and washed with water (2X) and brine. The organic layer was collected and dried over $MgSO_4$. Concentration in vacuo gave a white solid (0.71 g). The solid was purified by column chromatography (100 g silica gel, 5% MeOH/$CH_2Cl_2$ (500 ml)) gave the desired product as a white solid (0.29 g). NMR spectrum is consistent with structure (b) above.

(c)

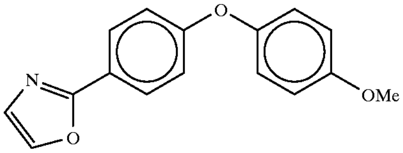

(c) A mixture of the compound of step b (0.149 g, 0.59 mmol) and $NiO_2$ (0.838 g, 8.9 mmol) in benzene (10 ml) was heated to reflux for 17 hours. The reaction was allowed to cool to room temperature and filtered through celite. Concentration of the filtrate gave a white solid (0.10 g). NMR spectrum is consistent with structure (c) above.

EXAMPLE 2

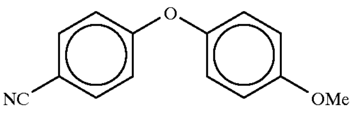

A mixture of 4-cyanophenol (1.856 g, 15.4 mmol) and potassium hydroxide (0.868 g, 14.1 mmol) was heated to 140° C. under argon. The resulting solution resolidified within 15 min. of heating. At this time, 4-iodoanisole (3.039 g, 12.8 mmol) was added followed by activated Cu (0.277 g) and the reaction mixture was heated to 170° C. for 20 hours. The reaction was allowed to cool to room temperature and 10% NaOH added. The mixture was extracted with $Et_2O$ (4×75 ml). The organic layers were collected, washed with brine and dried over $MgSO_4$. Concentration in vacuo gave a red/brown oil (0.68 g). The oil was purified by column chromatography (50 g silica gel; 5% EtOAc/hexane followed by 10% EtOAc/hexane) to give the product as a pale yellow solid (0.140 g). NMR spectrum is consistent with the structure above.

EXAMPLE 3

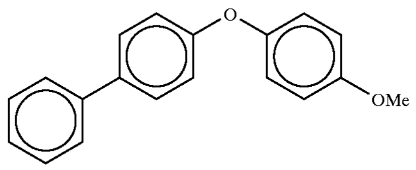

The procedures described in Example 2 were repeated using 4-phenylphenol (4.366 g, 25.6 mmol) in place of 4-cyanophenol, and 4-iodoanisole (5.053, g, 21.4 mmol). The reaction was heated to 200° C. for 3.5 hours. After work-up, a pale yellow solid was collected. The solid was recrystallized from MeOH to give the desired product (1.03 g). NMR spectrum is consistent with the structure above.

EXAMPLE 4

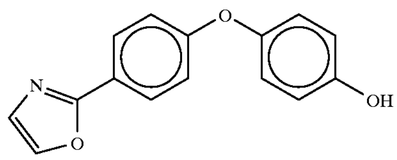

A solution of the compound of Example 1 (0.08 g, 0.3 mmol) in $CH_2Cl_2$ (2 Ml) was cooled to −78° C. A 1 M solution of $BBr_3$ in $CH_2Cl_2$ (0.66 ml) was added slowly under argon. The reaction was allowed to warm slowly to room temperature over 1.5 hours. The reaction was concentrated in vacuo and a mixture of water and $CH_2Cl_2$ was added to the residue. The organic layer was collected and washed with brine. Concentration in vacuo gave a brown oil (0.079 g). The oil solidified upon standing at room temperature. The solid was slurried with $CH_2Cl_2$ (3–5 ml) and the undissolved solid was collected by vacuum filtration to give a grey solid (0.047 g). NMR spectrum is consistent with the structure above.

EXAMPLE 5

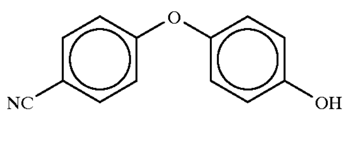

The procedures described in Example 4 were repeated using the compound of Example 2 (0.259 g, 1.2 mmol) in place of the compound of Example 1. After work-up, a blue solid was obtained as the desired product (0.262 g). NMR spectrum is consistent with the structure above.

EXAMPLE 6

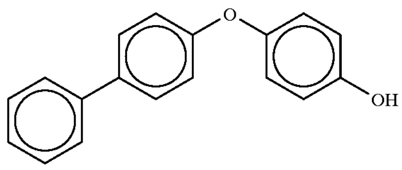

The procedures described in Example 4 were repeated using the compound of Example 3 (1.03 g, 3.7 mmol) in place of the compound of Example 1. Upon work-up, the desired product was obtained as a white solid (0.887 g). NMR spectrum is consistent with the structure above.

EXAMPLE 7

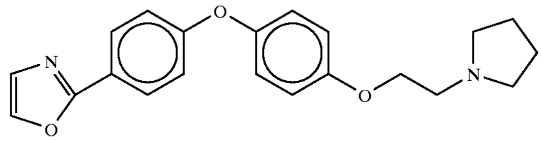

A mixture of the compound of Example 4 (0.04 g, 0.16 mmol), potassium carbonate (0.120 g, 0.79 mmol), and 1-(2-chloroethyl)pyrrolidine hydrochloride (0.037 g, 0.19 mmol) in DMF (3 ml) was heated to 80° C. (bath). After 21 hours of heating, the reaction was allowed to cool to room temperature and diluted with EtOAc (20 ml). The resulting solution was washed with water (2×20 ml) and brine (20 ml). The organic layer was collected, dried over $MgSO_4$, and concentrated in vacuo to give a white/yellow solid (0.04 g). The solid was purified by plate chromatography (5% MeOH/$CH_2Cl_2$) to give the desired product as a tan solid (0.022 g). Anal. calc'd for $C_{21}H_{22}N_2O_3$+0.2$H_2O$: C, 71.25; H, 6.38; N, 7.91. Found: C, 71.03; H, 5.98; N, 7.80. $M^+$=350.

EXAMPLE 8

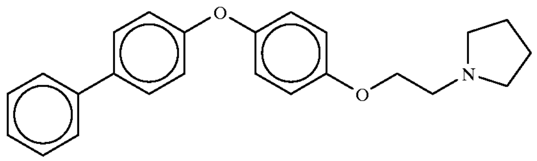

The procedures described in Example 7 were repeated using the compound of Example 6 (0.360 g, 1.4 mmol) in place of the compound of Example 4. After work-up, a yellow/white solid was obtained. The solid was further purified by slurrying with MeOH to give a cream-colored solid as the desired product (0.202 g). Anal. calc'd for $C_{24}H_{25}NO_2$+0.2 $H_2O$: C, 79.40; H, 7.05; N, 3.86. Found: C, 79.65; H, 7.11; N, 3.84. $MH^+$=360.

EXAMPLE 9

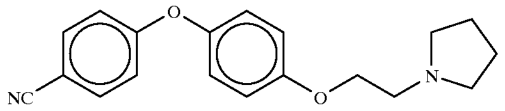

The procedures described in Example 7 were repeated using the compound of Example 5 (0.262 g, 1.2 mmol) in place of the compound of Example 4. After work-up, a yellow/brown oil was obtained as the desired product (0.260 g). NMR spectrum is consistent with the structure above.

EXAMPLE 10

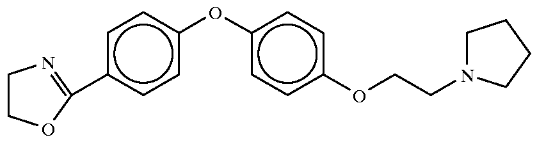

The procedures described in step b of Example 1 were repeated using the compound of Example 9 (0.087 g, 0.28 mmol) in place of the compound of Example 1 step a. After work-up, a yellow/white solid was obtained. The solid was further purified by column chromatography (95 $CHCl_3$: 5 EtOH: 0.5 $NH_4OH$) to give the desired product as a white solid (0.06 g). Anal. calc'd for $C_{21}H_{24}N_2O_3$+0.3 $H_2O$: C, 70.49; H, 6.93; N, 7.83. Found: C, 70.48; H, 7.02; N, 7.77. $MH^+$=353.

EXAMPLE 11

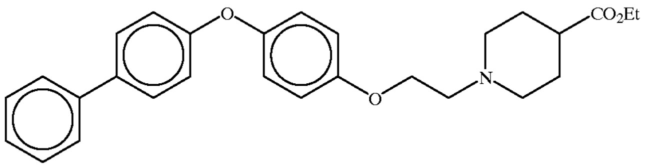

(a)

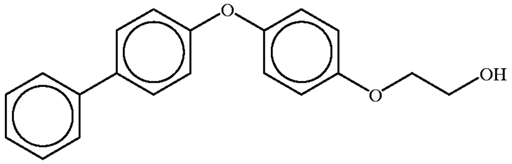

(a) To a solution of the compound of Example 6 (0.411 g, 1.6 mmol) in DMF (5 ml) was added ethylene carbonate (0.255 g, 2.9 mmol) and $nBu_4NBr$ (0.108 g, 0.31 mmol) under argon. The reaction was heated to 140–150° C. (bath). After 8 hours, additional ethylene carbonate (0.041 g) was added to the reaction. The reaction was stirred at 140–150° C. for an additional 16 hours before concentrating the reaction in vacuo. The resulting residue was dissolved in $CH_2Cl_2$ and washed with brine. The organic layer was collected, dried over $MgSO_4$, and concentrated in vacuo to give a light tan solid (0.570 g). The solid was recrystallized from EtOAc to give the desired product (0.210 g). NMR spectrum is consistent with the structure (a) above.

(b)

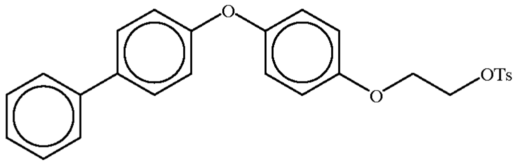

(b) A mixture of the compound from step a (0.085 g, 0.28 mmol) and TsCl (0.074 g, 0.36 mmol) in $CH_3CN$ (1.5 ml) was cooled to 0° C. Triethylamine (0.15 ml, 1.1 mmol) was then added neat under argon. The reaction was allowed to stir at 0° C. for 5 min. before removing the ice bath. The reaction was stirred at room temperature for 22 hours and then quenched with water. The resulting mixture was filtered and the desired product was collected as a tan solid. The solid was rinsed with $CH_3CN$/water (3:7) then allowed to air dry to give 0.107 g. The product was combined with 5 other previous runs and purified by column chromatography (3:1 hexane/EtOAc) to give the desired product as a white solid (0.142 g). NMR spectrum is consistent with the structure (b) above.

(c)

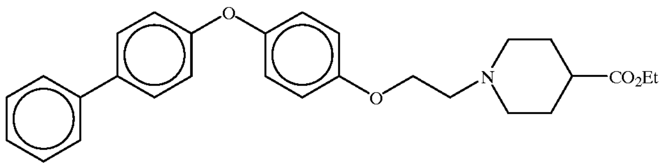

(c) To a solution of the compound from step b (0.142 g, 0.3 mmol) in DMF (1.5 ml) was added ethyl isonipecotate (0.05 ml, 0.3 mmol) followed by potassium carbonate (0.220 g, 1.5 mmol). The reaction mixture was heated to 80° C. (bath) under argon for 19.5 hours. The reaction was concentrated in vacuo and the residue was diluted with water (20 ml). The mixture was extracted with EtOAc (2x35 ml). The organic layers were combined, washed with brine, and dried over $MgSO_4$. Concentration in vacuo gave a white/yellow solid (0.134 g). The solid was purified by column chromatography (50 g silica gel, 1:1 EtOAc/hexane followed by 2:1 EtOAc/hexane) to give the desired product as a white solid (0.063 g). Anal. calc'd for $C_{28}H_{31}NO_4$: C, 75.48; H, 7.01; N, 3.14. Found: C, 75.28; H, 7.07; N, 3.09. $M^+$=445.

EXAMPLE 12

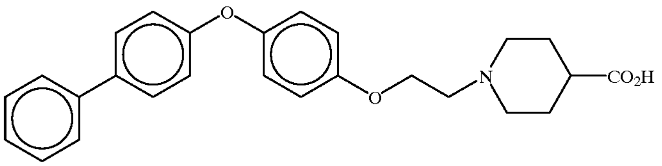

To a solution of the compound of Example 11 in distilled THF (5 ml) was added 6 M HCl. The reaction was heated to 85–95° C. for 2 hours. The reaction was then concentrated in vacuo to give a white solid. The solid was purified by slurrying with ether. A white solid was collected by vacuum filtration (0.014 g). Anal. calc'd for $C_{24}H_{25}NO_2$+3.0 HCl+1.0 $H_2O$: C, 57.31; H, 5.92; N, 2.57. Found: C, 57.37; H, 6.02; N, 2.25. $M^+$=417.

EXAMPLE 13

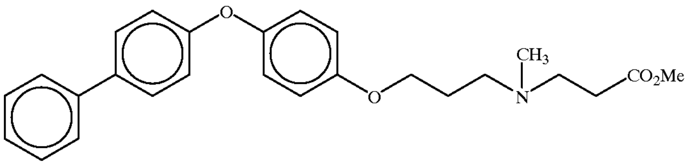

(a)

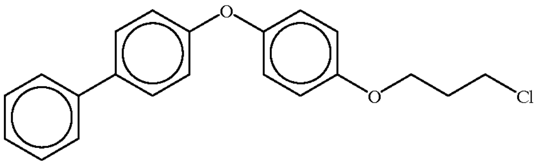

(a) To a solution of the compound of Example 6 (0.350 g, 1.3 mmol) in methyl ethyl ketone (4 ml) was added potassium carbonate (0.937 g, 6.7 mmol) followed by bromochloropropane (0.13 ml, 1.3 mmol) under argon. The resulting mixture was heated to 85–90° C. (bath) for 21.5 hours, then heated to 95° C. for 1.5 hours. The reaction was poured into a separatory funnel containing water (25 ml) and extracted with EtOAc (2x40 ml). The organic layers were combined, washed with brine, dried over $MgSO_4$, and concentrated in vacuo to give a yellow/white solid (0.442 g). The solid was purified by column chromatography (75 g silica gel, 5:1 hexane/EtOAC (500 ml)) to give the desired product as a white solid (0.324 g). NMR spectrum is consistent with structure (a) above.

(b)

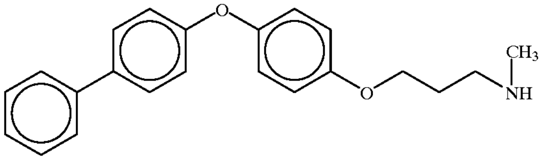

(b) To a mixture of the compound from step a (0.324 g, 0.96 mmol) in $CH_3CN$ (6 ml) was added $H_2NMe$ (8 ml, 95.6 mmol). Upon addition of $H_2NMe$, a white solid precipitated out of the mixture. The mixture was heated to 55° C. (bath) for 8.5 hours. At this time, additional $H_2NMe$ (2 ml) was added to the reaction. The reaction was stirred for another 16 hours at room temperature then heated to 55° C. for 3 hours. The reaction was concentrated in vacuo and extracted with EtOAc (2x20 ml). The organic layer was collected, cooled to 0° C., and acidified to pH 1 with 6 M HCl. At this point, no solid was observed to precipitate out of solution. The solution was therefore basified to pH 12 with 10% NaOH and extracted with EtOAc (2x50 ml). The organic layer was collected and dried over $MgSO_4$. Concentration in vacuo gave a white solid. The solid was slurried with EtOAc and collected by vacuum filtration as the desired product (0.224 g). NMR spectrum is consistent with the structure (b) above.

(c)

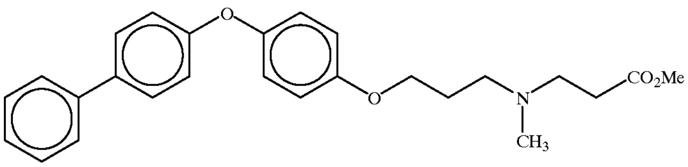

(c) To a solution of the compound of step b (0.224 g, 0.70 mmol) in $CH_2Cl_2$ (2 ml) was added methyl acrylate (0.08 ml, 0.91 mmol). The reaction was stirred at room temperature over 48 hours. At this time, additional methyl acrylate was added (0.04 ml) to the reaction. The reaction was stirred for another 3 hours, then concentrated under a stream of $N_2$ to give a white/yellow solid. The solid was purified by column chromatography (50 g silica gel, 10% MeOH/$CH_2Cl_2$ to give the desired product as a white solid (0.200 g). Anal. calc'd for $C_{26}H_{29}NO_4$: C, 74.44; H, 6.97; N, 3.34. Found: C, 74.11; H, 6.85; N, 3.21. $M^+$=419.

EXAMPLE 14

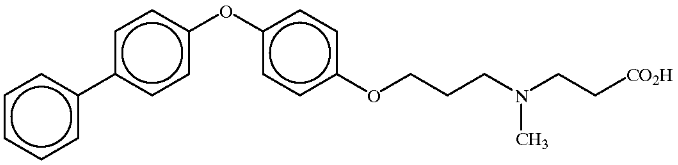

The compound of Example 13 (0.1 g) was treated with 6 M HCl under the same reaction conditions as those described in Example 12 to give the desired product as a white solid (0.073 g). $C_{25}H_{28}NO_4$+1.0 HCl+0.8 $H_2O$: C, 65.80; H, 6.54; N, 3.07. Found: C, 65.71; H, 6.25; N, 2.81. $MH^+$=406.

EXAMPLE 15

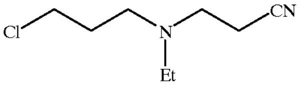

200 mL of 2N ethylamine in methanol (0.4 mol), 10 mL (0.15 mol) acrylonitrile and 35 mL (0.25 mol) triethylamine were stirred in 100 mL methanol at 25° C. for 21 hours. The mixture was concentrated and used without further purification. This was stirred in 70 mL DMF with 44 mL (0.44 mol) 1-bromo-3-chloropropane and 25 mL (0.18 mol) triethylamine at 40° C. for 5 hours and at 25° C. for 15 hours. The mixture was poured into water and ether and the ether layer was washed with 2N HCl. The acid layer was washed with ether, made basic (>pH 10) with 45% KOH and extracted twice with ether. The ether extracts were dried over $Na_2SO_4$ and concentrated to provide the desired compound (21.7 g, 0.124 mol) as a colorless oil: $^1H$ NMR ($CDCl_3$) δ1.04 (t,3H), 1.88 (m, 2H), 2.40–2.65 (m, 6H), 3.65 (t, 2H).

EXAMPLE 16

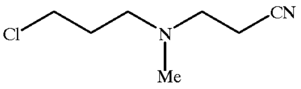

The compound was prepared as described for Example 15, using a solution of methylamine in place of ethylamine.

EXAMPLE 17

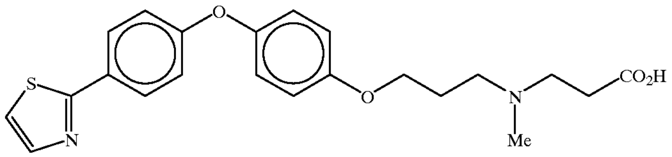

(a)

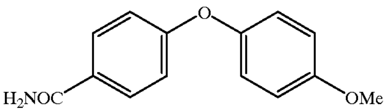

(a) To a suspension of the product from Example 2 (10.0 g, 44 mmol) in t-butanol (80 mL) was added 30 mL dimethylsulfoxide (DMSO) and powdered KOH (9.1 g, 162 mmol). The mixture was heated at reflux for 2 hours. The mixture was cooled and diluted with water (100 mL). The white solid precipitate was collected by filtration and washed with water (4×150 mL). The solid was dried in vacuo to give 9.6 g (89%) of (a): mp 195–196° C.

(b)

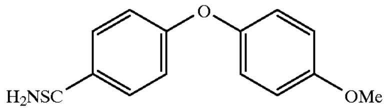

(b) To a suspension of the compound from step (a) (4.2 g, 17.3 mmol) in toluene (80 mL) was added Lawesson's reagent (7.0 g, 17.3 mmol). The mixture was heated at reflux for 3 hours, cooled and concentrated in vacuo. The residue was chromatographed on silica gel (1:1 hexane/ethyl acetate) to give 2.2 g (49%) of (b).

(c)

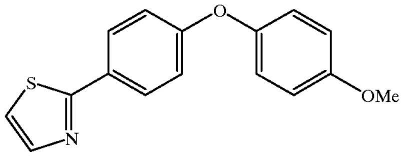

(c) A mixture of oxalic acid (590 mg, 6.5 mmol) and chloroacetaldehyde dimethyl acetal (0.75 mL, 6.5 mmol) was heated at reflux for 1 hour. The oil bath was removed for 10 minutes and the compound from step (b) (1.7 g, 6.5 mmol) was added. The resulting mixture was heated at reflux for 2 hours. The mixture was cooled to room temperature and 30% HCl (3.5 mL) was added. The mixture was heated at reflux for 10 minutes, cooled and diluted with water. The reaction mixture was extracted with $CH_2Cl_2$ (3×10 mL). The organic solution was dried ($Na_2SO_4$) and concentrated in vacuo. The residue was chromatographed (3:1 hexane/ethyl acetate) to give the 925 mg (50%) of (c) as a crystalline solid: mp 92–93° C.; Anal. calcd for $C_{16}H_{13}NO_2S$: C, 67.82; H, 4.62; N, 4.94. Found: C, 67.66; H, 4.50; N, 4.86.

(d)

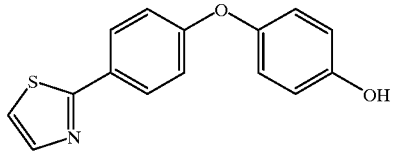

(d) To a solution of the compound from step (c) (280 mg, 1.0 mmol) in $CH_2Cl_2$ (3 mL) at −78° C. was added boron tribromide (1.8 mL of a 1M solution in $CH_2Cl_2$). The solution was kept at −78° C. for 1 h and then warmed to room temperature over 2 hours. The reaction solution was diluted with water and extracted with $CH_2Cl_2$ (2×20 mL). The combined organic solution was dried ($Na_2SO_4$) and concentrated in vacuo to give 210 mg (78%) of (d).

(e)

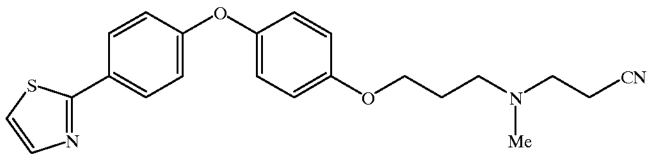

(e) To a suspension of powdered KOH (63 mg, 1.1 mmol) in DMSO (1 mL) as added via canula a solution of the compound from step (d) (200 mg, 0.74 mmol) in DMSO (2 mL). The mixture was stirred at room temperature for 5 min and the product of Example 16 (118 mg, 0.74 mmol) in DMSO (1 mL) was added via canula. The reaction mixture was heated at 45° C. for 4 hours. The mixture was cooled to room temperature and partitioned between water and ether (15 mL). The aqueous solution was extracted with ether (2×10 mL). The combined organic solution was dried ($Na_2SO_4$) and concentrated in vacuo. The residue was chromatographed (ethyl acetate) to give 112 mg (39%) of (e) as a crystalline solid: mp 63–64° C.

(f)

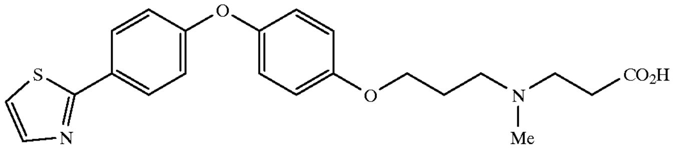

(f) A solution of the compound from step (e) (100 mg, 0.25 mmol) in 6N HCl (2 mL) was heated at 90° C. for 17 hours. The solution was cooled to room temperature and brought to pH 8 with 10% NaOH. The aqueous solution was extracted with $CH_2Cl_2$ (3x15 mL). The organic solution was concentrated in vacuo. The residue as chromatographed on silica (85:14:1 $CH_2Cl_2$/MeOH/$NH_4OH$) to give 40 mg (39%) of (f) as a crystalline solid: mp 143–144° C.

EXAMPLE 18

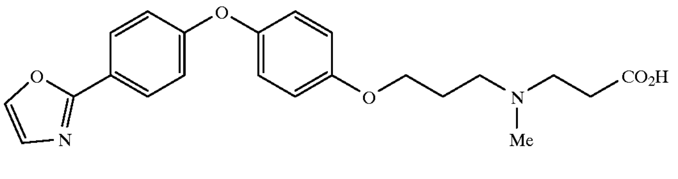

The product from Example 4 (434 mg, 1.7 mmol), the product from Example 16 (305 mg, 1.9 mmol) and powdered KOH (158 mg, 2.8 mmol) were stirred in 20 mL DMF at 50° C. for 12 hours. The mixture was cooled and diluted with 75 mL $H_2O$. The aqueous base was separated and extracted with 3x25 mL methyl t-butyl ether (MTBE). The combined organic phases were dried ($MgSO_4$) and concentrated to afford the crude product as a brown oil. The crude nitrile was dissolved in 5 mL MTBE and 5 mL concentrated HCl was added. The MTBE was distilled from the reaction and an additional 2 mL concentrated HCl was added. The reaction was heated to 95° C. for 24 hours. After cooling, the mixture was diluted with 50 mL $H_2O$ and neutralized with a saturated $NaHCO_3$ solution. The aqueous phase was extracted with 4x15 mL $CH_2Cl_2$ and the extracts dried ($MgSO_4$) and concentrated to afford a yellow oil. The oil was dissolved in 1 mL methanol and 3M ethanolic HCl was added until a precipitate formed. The tan solid was filtered and dried: Anal. calcd for $C_{22}H_{24}N_2O_5$●1.5 HCL●1.0 $H_2O$: C. 56.32; H, 5.91; N, 5.97; Cl, 11.34. Found: C, 56.61; H, 5.75; N, 5.32; Cl, 11.55.

EXAMPLE 19

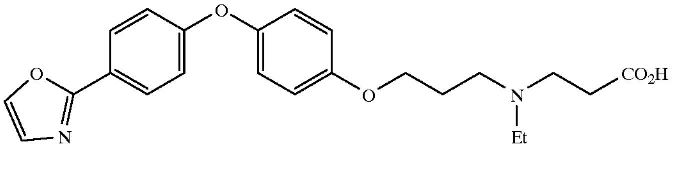

The above compound was prepared in the same manner as Example 18 substituting the product from Example 15 in place of the product of Example 16. The HCl salt was isolated as a tan solid: Anal. calcd for $C_{23}H_{26}N_2O_5$●1.25 HCl●1.0 $H_2O$: C, 58.27; H, 6.22; N, 5.91; Cl, 9.35. Found: C, 58.16; H, 6.25; N, 5.26; Cl, 9.14.

LTA Hydrolase Methods

The following Table presents data demonstrating the pharmacological activity of the LTA hydrolase inhibitors of the present invention. One or more of three different assays, (1) an in vitro LTA hydrolase enzyme assay, (2) a human whole blood assay utilizing calcium ionophore stimulation, and (3) a murine ex vivo assay utilizing calcium ionophore stimulation were employed to determine the level of LTA hydrolase inhibitor activity.

Recombinant Human LTA Hydrolase Assay for LTA Hydrolase Inhibitor Activity

Compounds of the present invention were tested for LTA hydrolase inhibitor activity against recombinant human LTA hydrolase (rhLTAH). Recombinant human LTA hydrolase-encoding vectors were prepared and used to express rhLTAH essentially as described by J. Gierse, et al., *Protein Expression and Purification,* 4, 358–366 (1993). Briefly, LTA hydrolase encoding DNA was amplified by polymerase chain reaction using a pair of oligonucleotide primers based on the nucleotide sequence from the 5'-end, and the complement of the 3'-end, of the coding region of the LTA hydrolase gene, the nucleotide sequence of which gene is known. (See, C. Funk, et al., Proc. Natl. Acad. Sci. USA 84, 6677–6681 (1987)). A λgt11 human placental cDNA library (Clonetech, Palo Alto, Calif.) provided the nucleic acid template. The LTA hydrolase encoding region had a length of about 1.9 kb. The amplified 1.9 kb DNA was isolated and cloned into the genomic baculovirus, *Autographa californica* nuclear polyderosis virus (AcNPC) DNA, and the baculovirus expression vector was transfected into *Spodoptera frugiperda* Sf-9 cells employing the calcium phosphate co-precipitation method (see, M. Summers, et al., Tex. Agric. Exp. Stn. Bull. 1555, 1–57 (1987). Recombinant $LTA_4$ hydrolase enzyme was purified from the transfected Sf-9 cells essentially as described by J. Gierse, et al., supra.

One or more predetermined amounts of a compound of the invention were incubated in assay buffer (0.1 M potassium phosphate, 5 mg/ml fatty acid free BSA, 10% DMSO, Ph 7.4) for 10 minutes at room temperature with 250 ng of recombinant $hLTA_4H$ to allow binding, if any, between the enzyme and inhibitor. The stock enzyme solution was 1 mg/m. $LTA_4$ hydrolase, 50 Mm Tris, Ph 8.0, 150 Mm NaCl, 2.5 Mm beta-mercaptoethanol, 50% glycerol. The specific activity of the enzyme was about 650 Nmoles/min/mg. $LTA_4$ (i.e., substrate) was prepared from the methyl ester of $LTA_4$ (Biomol, Inc., Plymouth Meeting, Pa.) by treating the methyl ester with 30 molar equivalents of LiOH at room temperature for 18 hours. The $LTA_4$ substrate in its free acid form was kept frozen at −80° C. until needed. $LTA_4$ (free acid) was thawed and diluted in assay buffer (minus DMSO) to a concentration of 350 ng/ml and 25 μl (8 ng) of LTA4 substrate was added to the reaction mixture (total volume of reaction mixture=200 μl at time zero. Each reaction was carried out at room temperature for 10 minutes. The reaction was stopped by diluting 25 μl of the reaction mixture with 500 μl of the assay buffer without DMSO. $LTA_4$ was quantified in the diluted sample by a commercially available enzyme-linked immunoassay [Caymen Chemical Col. Ann Arbor, Mich.] using the method recommended in the manufacturer's instructions and compared to the amount of $LTA_4$ produced in a negative control (i.e., essentially identical conditions except without addition of an inhibitor compound). The $IC_{50}$ was routinely calculated from the data produced.

$LTB_4$ and Thromboxane Production by Calcium Ionophore Stimulated Human Blood for $LTB_4$ Hydrolase Inhibitor Activity Human blood, collected in heparin-containing Vacutainer tubes, was diluted 1:4 with RPMI-1640 media and 200 μl of the diluted blood was added into each of a 96-well microtiter plate. One or more concentrations of the leukotriene $A_4$ hydrolase inhibitor compounds being tested were prepared (diluted in DMSO) and 2 μl added and gently mixed with the diluted whole blood. After incubating for 15 minutes at 37° C. in a humidified incubator, calcium ionophore A13187 (Sigma Chemical Co., St. Louis, Mo.) was added to a final concentration of 20 mcg/ml and the incubation continued under the same conditions for an additional 10 minutes to allow $LTB_4$ formation. The reaction was terminated by centrifugation (833 g, 10 minutes at 4° C.) and supernatant were analyzed for $LTB_4$ and thromboxane by commercially available enzyme-linked immunoassays (Caymen Chemical Co., Ann Arbor, Mich.) according to the manufacturer's instructions. The $IC_{50}$ of each test compound was determined from the amount of inhibition of $LTB_4$ production as compared to an essentially identical assay in which no inhibitor compound was present.

Ex Vivo $LTB_4$ and Thromboxane Production by Calcium Ionophore Stimulated Mouse Blood for $LTB_4$ Hydrolase Inhibitor Activity Leukotriene $A_4$ hydrolase inhibitor compounds of the present invention were diluted to a predetermined concentration in phosphate buffered saline containing 2% DMSO and 1% Tween 80. The compounds were administered by oral gavage to adult male outbred mice weighing approximately 20–30 gm at a dose of 10 mg/kg body weight. (Compounds given at a dose of 50 mg/kg body weight are designated in following Table by the symbol, *) Sixty (60) minutes after administration of an $LTA_4$ inhibitor compound of the invention, blood was collected (into heparin-containing tubes) from the retroorbital sinus. The heparinized blood was added to the wells of a microtiter plate along with an equal volume of RPMI-1640 media, and calcium ionophore A23187 was added to a final concentration of 20 mcg/ml. The mixture was incubated for 10 minutes at 37° C. in a humidified incubator. The reaction was terminated by centrifugation (833 g. 10 minutes at 4° C.). Supernatant were analyzed for $LTB_4$ and thromboxane by commercially available enzyme-linked immunoassays [Caymen Chemical Co., Ann Arbor, Mich.] in accordance with the manufacturer's instructions. The percent inhibition was determined by comparison to animals treated identically except that the solution administered by oral gavage was devoid of inhibitor compound.

$LTA_4$ HYDROLASE INHIBITOR ACTIVITY

| Ex. # | Recombinant Human $LTA_4$ Hydrolase Assay $IC_{50}$ (μM) | Inhibition of Calcium Ionophore-induced $LTB_4$ Production in Human Blood $IC_{50}$ (μM) | Murine Ex Vivo $LTB_4$ Inhibition % I $LTB_4$/at 1 hour after administration of 10 mg/kg |
|---|---|---|---|
| 7 | 0.43 | 0.55 | 93% |
| 8 | 0.0066 | 0.14 | 57% |
| 10 | 0.59 | 0.55 | 83% |
| 11 | 0.34 | 0.72 | 90% |
| 12 | — | 0.22 | 87% |
| 13 | 0.55 | 0.79 | 63% |
| 14 | <0.0005 | 0.19 | 78% |
| 17 | 0.95 | 0.072 | 87% |
| 18 | 0.027 | 0.19 | 94% |
| 19 | 0.34 | 0.24 | 93% |

"—" means Not Determined

What is claimed is:

1. A compound having the structure:

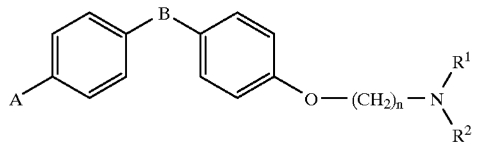

wherein:

A is

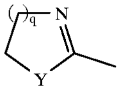

wherein

..... represents a single or double bond;

q is 1

Y is —CH— or —$CH_2$—

B is —O—, —$CH_2$— or —$CH_2O$— n is 2 to 4

$R^1$ is H or $C_1$ to $C_4$ alkyl $R^2$ is $(CH_2)_m$ $R^3$ wherein m is 1 to 3

$R^3$ is $CO_2R^4$ $R^4$ is H, alkyl, amino, alkylamino, dialkylamino; or $NR^1R^2$ is combined to form

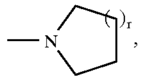,
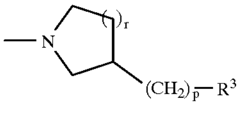
or
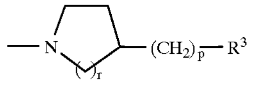

wherein r is 1 or 2, p is 0 to 3 and $R^3$ is as defined above.

2. The compound of claim 1 wherein B is —O—.

3. The compound of claim 2 wherein $NR^1R^2$ is combined to form

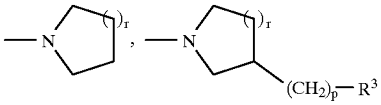
or

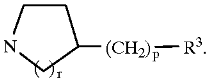

4. A pharmaceutical composition comprising compound having the structure:

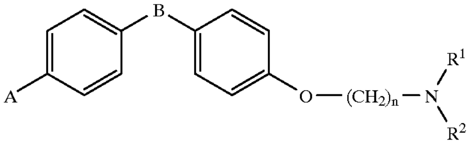

or a pharmaceutically acceptable salt or stereoisomer thereof, and a pharmaceutically acceptable carrier, wherein A is

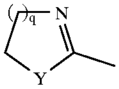

wherein

..... represents a single or double bond q is 1

Y is —CH— or —$CH_2$—

B is —O—, —$CH_2$— or —$CH_2O$— n is 2 to 4

$R^1$ is H or $C_1$ to $C_4$ alkyl $R^2$ is $(CH_2)_m$ $R^3$ wherein m is 1 to 3

$R^3$ is $CO_2R^4$ $R^4$ is H alkyl, amino, alkylamino, dialkylamino or $NR^1R^2$ is combined to form

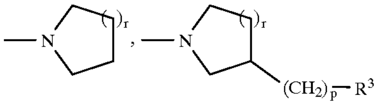
or

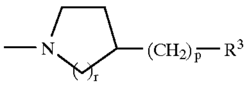

wherein r is 1 or 2, p is 0 to 3 and $R^3$ is as defined above.

5. The pharmaceutical composition of claim 4 wherein in the compound B is —O—.

6. The pharmaceutical composition of claim 5 wherein in the compound $NR^1R^2$ is combined to form

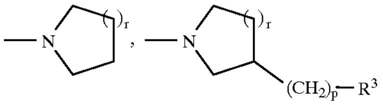
or

-continued

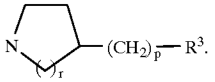

7. A method for treating an $LTB_4$-mediated inflammatory disease comprising administering to a mammal in need of treatment a therapeutically effective amount of a compound having the structure:

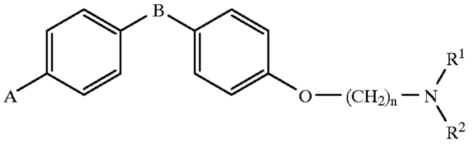

or a pharmaceutically acceptable salt or stereoisomer thereof, and a pharmaceutically acceptable carrier, wherein A is

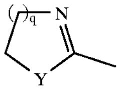

wherein

..... represents a single or double bond q is 1

Y is —CH— or —$CH_2$—

B is —O—, —$CH_2$— or —$CH_2O$— n is 2 to 4

$R^1$ is H or $C_1$ to $C_4$ alkyl $R^2$ is $(CH_2)_m$ $R^3$ wherein m is 1 to 3

$R^3$ is $CO_2R^4$ $R^4$ is H alkyl, amino, alkylamino, dialkylamino or $NR^1R^2$ is combined to form

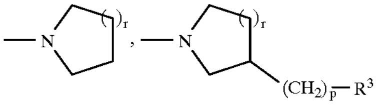
or

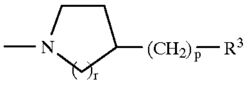

wherein r is 1 or 2, p is 0 to 3 and $R^3$ is as defined above.

8. The method of claim 7 wherein in the structure of the compound B is —O—.

9. The method of claim 8 wherein in the structure of the compound $NR^1R^2$ is combined to form

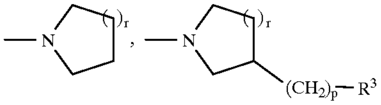
or

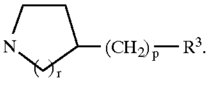

* * * * *

UNITED STATES PATENT AND TRADEMARK OFFICE
CERTIFICATE OF CORRECTION

PATENT NO. : 5,925,654

DATED : July 20, 1999

INVENTOR(S) : BARBARA BAOSHENG CHEN ET AL.

It is certified that error appears in the above-identified patent and that said Letters Patent is hereby corrected as shown below:

ON THE COVER PAGE [54]:

The title, "$LTA_4$," should read --$LTA_4$--.

COLUMN 1:

Line 1, "$LTA_4$," should read --$LTA_4$--.

COLUMN 4:

Line 19, "inventio" should read --invention--;
Line 20, "ncan" should read --can--; and
Line 21, "like For" should read --like. For--.

COLUMN 9:

Line 63, "4 hours The" should read --4 hours. The--.

COLUMN 11:

Line 15, "(5.053,g," should read --(5.053g,--.

COLUMN 18:

Line 20, "(t,3H)," should read --(t, 3H),--.

UNITED STATES PATENT AND TRADEMARK OFFICE

CERTIFICATE OF CORRECTION

PATENT NO. : 5,925,654

DATED : July 20, 1999

INVENTOR(S) : BARBARA BAOSHENG CHEN ET AL.

It is certified that error appears in the above-identified patent and that said Letters Patent is hereby corrected as shown below:

COLUMN 22:

Line 61, "LTA4" should read --$LTA_4$--.

Signed and Sealed this

Twenty-fourth Day of October, 2000

Attest:

Q. TODD DICKINSON

*Attesting Officer*

*Director of Patents and Trademarks*